(12) United States Patent
Jiang et al.

(10) Patent No.: US 8,450,054 B2
(45) Date of Patent: *May 28, 2013

(54) **MODIFIED *LUCIOLA CRUCIATA* LUCIFERASE GENE AND PROTEIN**

(75) Inventors: Ying Jiang, Eugene, OR (US); Daniel J. Coleman, Corvallis, OR (US); John J. Naleway, Eugene, OR (US); Gabriele M. Cook, Eugene, OR (US)

(73) Assignee: Marker Gene Technologies, Inc., Eugene, OR (US)

( * ) Notice: Subject to any disclaimer, the term of this patent is extended or adjusted under 35 U.S.C. 154(b) by 294 days.

This patent is subject to a terminal disclaimer.

(21) Appl. No.: 12/928,337

(22) Filed: Dec. 9, 2010

(65) Prior Publication Data

US 2012/0028257 A1 Feb. 2, 2012

Related U.S. Application Data

(60) Continuation-in-part of application No. 12/800,830, filed on May 24, 2010, now Pat. No. 8,206,961, which is a division of application No. 12/287,561, filed on Oct. 10, 2008, now Pat. No. 7,723,502.

(51) Int. Cl.
*C12Q 1/00* (2006.01)
*C12Q 1/66* (2006.01)

(52) U.S. Cl.
USPC .................................................. 435/4; 435/8

(58) Field of Classification Search
None
See application file for complete search history.

(56) References Cited

PUBLICATIONS

Masuda et al. (Cloning and sequence analysis of cDNA for luciferase of a Japanese firefly, *Luciola cruciata*, Gene 77: 265-270, 1989).*

* cited by examiner

*Primary Examiner* — Suzanne M Noakes
*Assistant Examiner* — Jae W Lee
(74) *Attorney, Agent, or Firm* — Timothy L. McCutcheon

(57) ABSTRACT

A codon optimized and stabilized luciferase gene based upon the sequence of the natural luciferase gene isolated from *Luciola cruciata* (Japanese firefly) and a novel recombinant DNA characterized by incorporating this new gene coding for a novel luciferase into a vector DNA for improved activities in mammalian cells, are disclosed. This new luciferase exhibits long-wavelength light emission, as well as improved thermostability and higher expression levels in mammalian cell systems, compared to native luciferase. Assays using this new enzyme for measuring various biological metabolic functions are described.

12 Claims, 10 Drawing Sheets

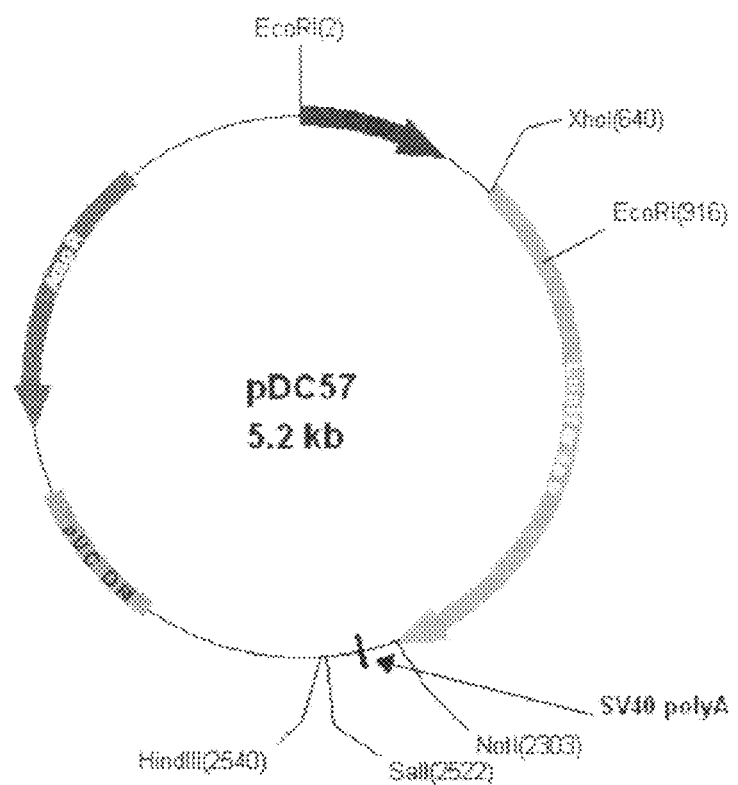
Figure 1. Cleavage map of recombinant plasmid pDC57 DNA with elements and endonuclease restriction enzymes sites listed.

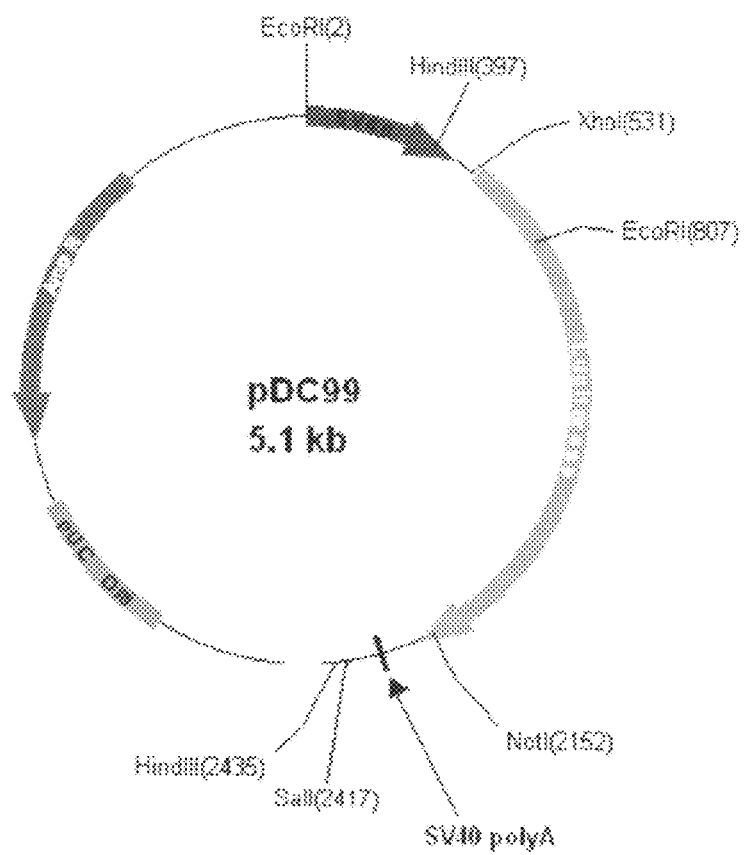
Figure 2. Cleavage map of recombinant plasmid pDC99 DNA with elements and endonuclease restriction enzymes sites listed.

Figure 3. Comparison of native *L. cruciata* luciferase sequence with codon optimized nucleotide sequence of the present invention (changes from native sequence in bold/underline).

```
   1   ATGGAAAATATGGAAAACGACGAGAACATCGTGGTGGGCCCCAAGCCCTT
  51   CTACCCCATCGAGAAGGCAGCGCCGGCACCCAGCTGCGGAAGTACATGG
 101   AAAGATACGCCAAGCTGGGCGCCATTGCCTTCACCAACGCCGTGACCGGC
 151   GTGGACTACAGCTACGCCGAGTACCTGGAAAAGAGCTGCTGCCTGGGCAA
 201   GGCTCTGCAGAACTACGGCCTGGTGGTGGACGGCCGGATCGCCCTGTGCA
 251   GCGAGAACTGCGAGGAATTCTTCATCCCCGTGATCGCCGGCCTGTTCATC
 301   GGCCTGGGCGTGGCTCCCACCAACGAGATCTACACCCTGCGGGAGCTGGT
 351   GCACAGCCTGGGCATCAGCAAGCCCACCATCGTGTTCAGCAGCAAGAAGG
 401   GCCTGGACAAAGTCATCACCGTGCAGAAAACCGTGACCACCATCAAGACC
 451   ATCGTGATCCTGGACAGCAAGGTGGACTACCGGGGCTACCAGTGCCTGGA
 501   CACCTTCATCAAGCGGAACACCCCGCCTGCCTTCCAGCCCAGCAGCTTCA
 551   AGACCGTGGAGGTGGACTGGAAAGAACAGCGTGGCCCTGATCATGAACAGC
 601   AGCGGCAGCACCGGCCTGCCCAAGGGCGTGCAGCTGACCCACGAGAACAC
 651   CGTGACCCGGTTCAGCCACGCCAGGGACCCCATCTACGGCAACCAGGTGT
 701   CCCCCGGTACCGCCGTGCTGACCGTGGTGCCCTTCCACCACGGCTTCGGC
 751   ATGTTCACCACCCTGGGCTACCTGATCTGCGGCTTCCGGGTGGTGATGCT
 801   GACCAAGTTCGACGAGGAAACCTTCCTGAAAACCCTGCAGGACTACAAGT
 851   GCACCTACGTGATTCTGGTGCCCACCCTGTTCGCCATCCTGAACAAGAGC
 901   GAGCTGCTGAACAAGTACGACCTGAGCAACCTGGTGGAGATCGCCAGCGG
 951   CGGAGCCCCCCTGAGCAAAGAAGTGGAGAGCCGTCGCCAGGCGGTTCA
1001   ATCTGCCCGGCGTGCGGCAGGGCTACGGCCTGACCGAGACAACCAGCGCC
1051   ATCATCATCACCCCGAGGGCGACGACAAGCCTGGAGCCAGCCGGCAAGGT
1101   GGTGCCCCTGTTCAAGGCCAAAGTGATCGACCTGGACACCAAGAAGAGCC
1151   TGGCCCCCAACAGACGGCGCGAAGTGTGCGTGAAGGGCCCTCATGCTGATG
1201   AAGGCCTACGTGAACAACCCCGAGGCCACCAAAGAGTTGATCGACGAAGA
1251   GGGCTGGCTGCACACCGGCGACATCGGCTACTACGACGAAGAGAAGCACT
1301   TCTTCATCGTGGACCGGCTGAAGAGCCTGATCAAGTACAAGGGCTATCAG
1351   GTGGCCCCTGCCGAGCTGGAAAGCGTCCTGCTGCAGCACCCCAGCATCTT
1401   CGACGCCGGCGTGGCCGGGTGCCAGATCCTGTGGCCGGCGAGCTGCCTG
1451   GCCGCGGTGGTGCTGGAATCCGCAAGAACATGACCGAGAAAGAAGTG
1501   ATGGACTACGTCGCCAGCCAGGTGTCCAACGCCAAGCGGCTGAGAGGCGG
1551   CGTGACATTCGTGGACGAAGTGCCAAAGGGCCTGACCGGCAAGATCGACG
1601   GCAGGGCCATCCGGGAGATCCTGAAGAAACCCGTGGCCAAGATG
```

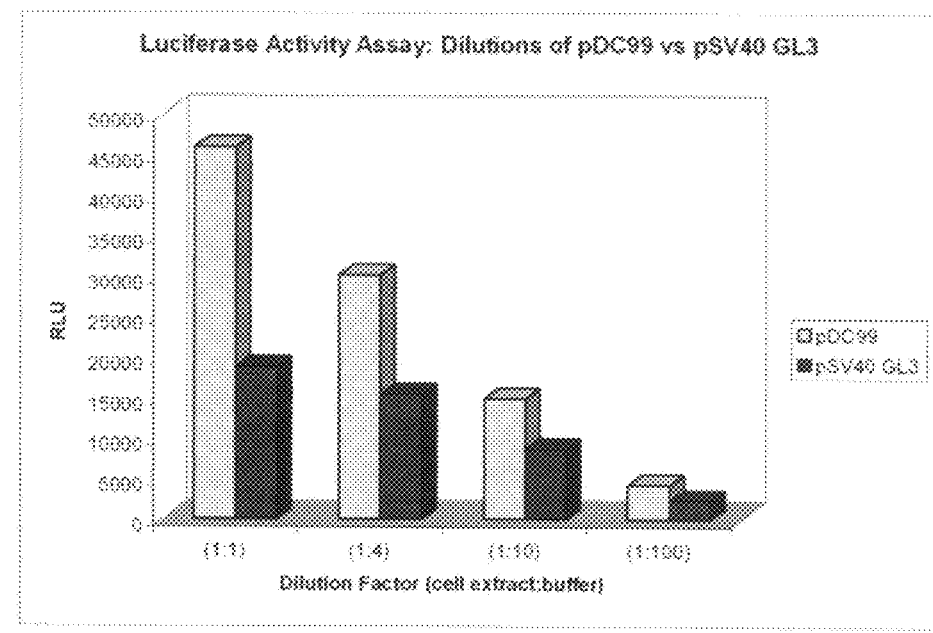
Figure 4. Analysis of Luciferase Expression Levels using the pDC99 Vector and Comparison to the Luciferase Expression Using the *Photinus pyralis* luciferase Vector pSV40-GL3 in mammalian cells.

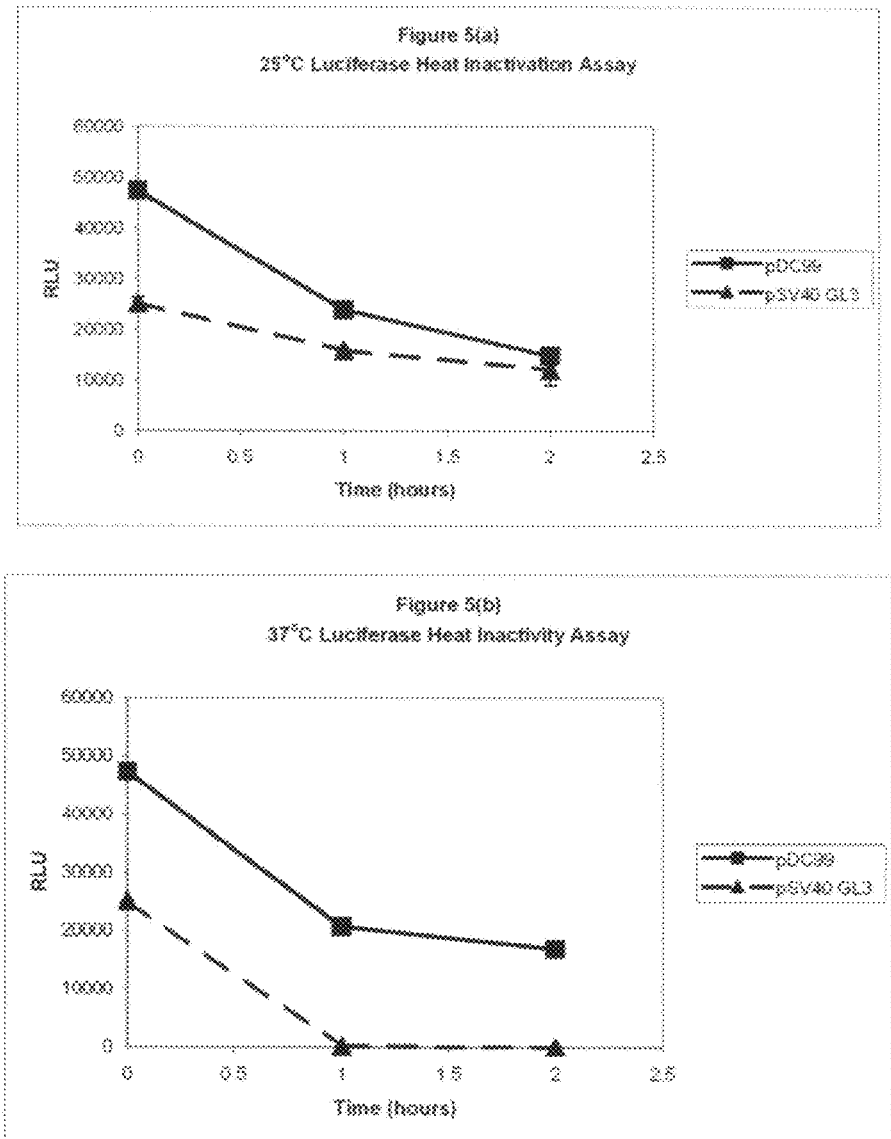
Figure 5. Analysis of the thermal stability of the modified *Luciola cruciata* luciferase protein versus the *Photinus pyralis* wild type protein (a) at 25°C and (b) at 37°C.

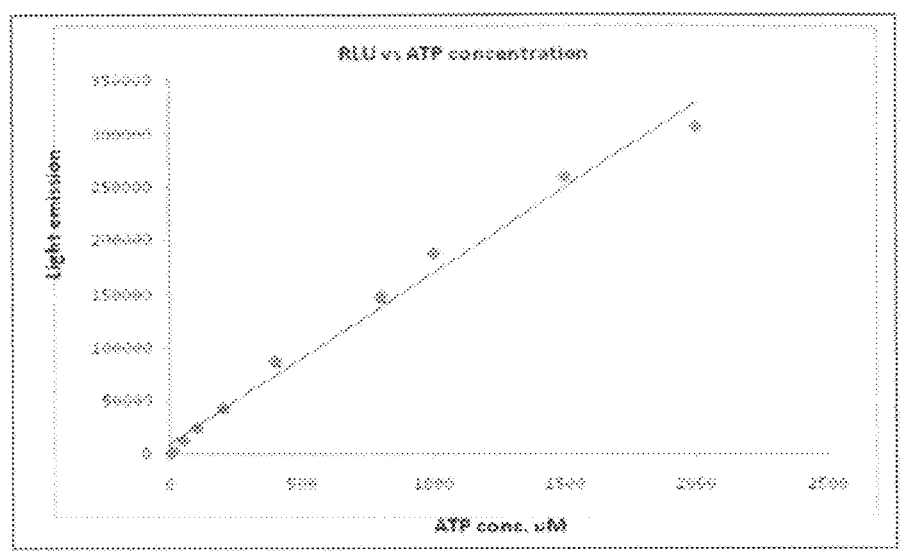
Figure 6. The modified recombinant luciferase protein SEQ ID NO:4 can be used to quantitatively measure ATP concentration.

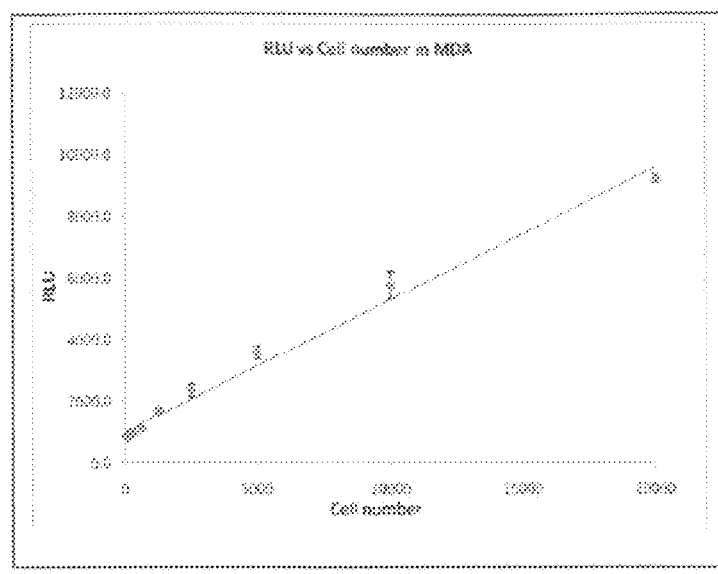
Figure 7. The modified recombinant luciferase protein SEQ ID NO:4 can be used to quantitatively measure the number of cells present in culture samples.

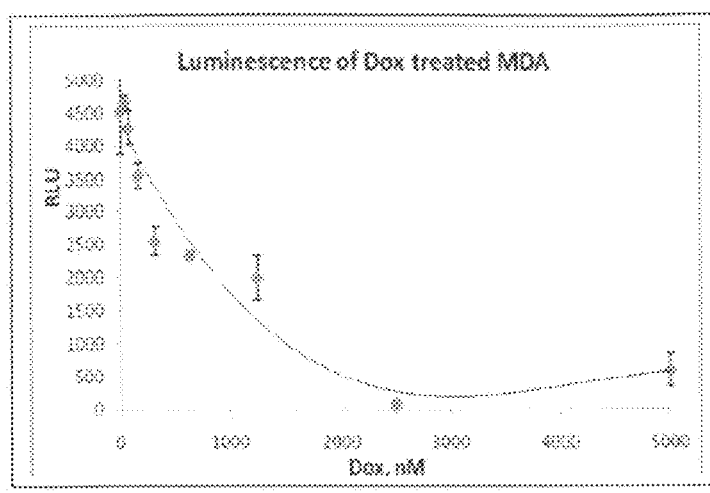
Figure 8. The modified recombinant luciferase protein SEQ ID NO:4 can be used to measure cell viability

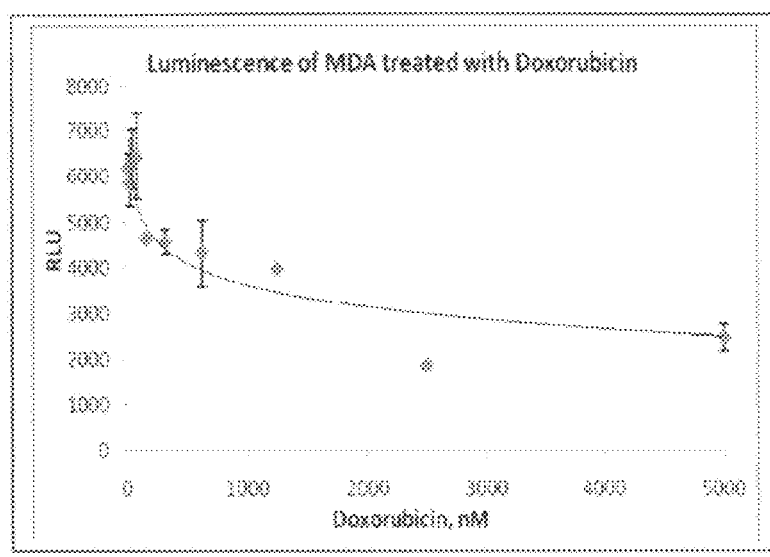
Figure 9. The modified recombinant luciferase protein SEQ ID NO:4 can be used to measure cell cytotoxicity upon drug treatment

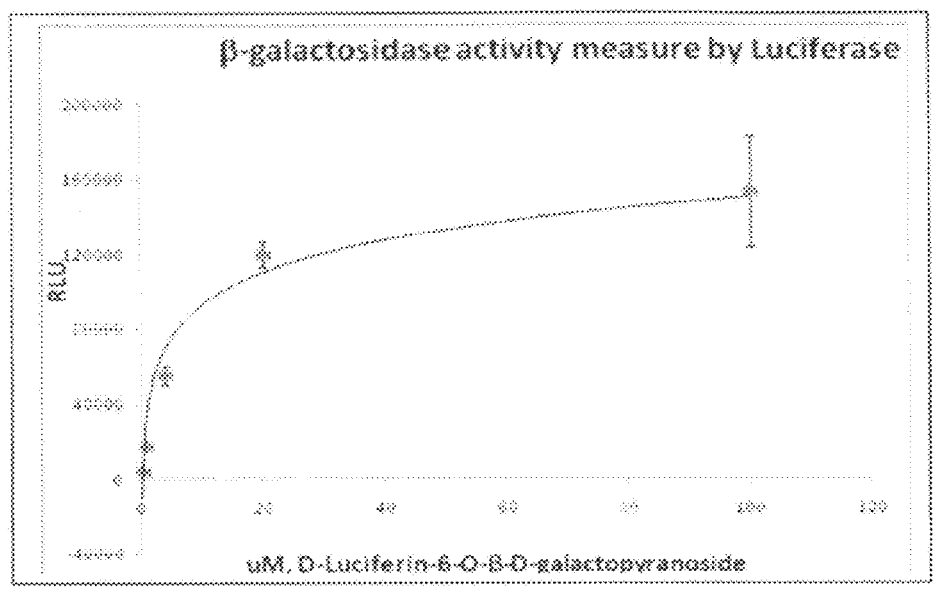
Figure 10. The modified recombinant luciferase protein SEQ ID NO 4 can be used to measure a second enzyme, β-galactosidase, in a coupled assay format.

SEQUENCE LISTING

```
<160> NUMBER OF SEQ ID NOS: 24

<210> SEQ ID NO 1
<211> LENGTH: 1644
<212> TYPE: DNA
<213> ORGANISM: Luciola cruciata

<400> SEQUENCE: 1
atggaaaaca tggaaaacga tgaaaatatt gtagttggac ctaaaccgtt ttaccctatc      60
```

```
gaagagggat ctgctggaac acaattacgc aaatacatgg agcgatatgc aaaacttggc    120
gcaattgctt ttacaaatgc agttactggt gttgattatt cttacgccga atacttggag    180
aaatcatgtt gtctaggaaa agctttgcaa aattatggtt tggttgttga tggcagaatt    240
gcgttatgca gtgaaaactg tgaagaattt tttattcctg taatagccgg actgtttata    300
ggtgtaggtg ttgcacccac taatgagatt tacactttac gtgaactggt tcacagttta    360
ggtatctcta aaccaacaat tgtatttagt tctaaaaaag cttagataaa agttataaca    420
gtacagaaaa cagtaactac tattaaaacc attgttatac tagatagcaa agttgattat    480
cgaggatatc aatgtctgga cacctttata aaaagaaaca ctccaccagg ttttcaagca    540
tccagtttca aaactgtgga agttgaccgt aaagaacaag ttgctcttat aatgaactct    600
tcggttctaa ccggttttgcc aaaaggcgta caacttactc acgaaaatac agtcactaga    660
ttttctcatg ctagagatcc gatttatggt aaccaagttt caccaggcac cgctgtttta    720
actgtcgttc cattccatca tggttttggt atgttcacta ctctagggta tttaatttgt    780
ggttttcgtg ttgtaatgtt aacaaaattc gatgaagaaa catttttaaa aactctacaa    840
gattataaat gtacaagtgt tattcttgta ccgaccttgt ttgcaattct caacaaaagt    900
gaattactca ataaatacga tttgtcaaat ttagttgaga ttgcatctgg cggagcacct    960
ttatcaaaag aagttggtga agctgttgct agacgcttta atcttcccgg tgttcgtcaa   1020
ggttatggtt aacagaaac aacatctgcc attattatta caccagaagg agacgataaa   1080
ccaggagctt ctggaaaagt cgtgccgttg tttaaagcaa aagttattga tcttgatacc   1140
aaaaaatctt taggtcctaa cagacgtgga gaagtttgtg ttaaaggacc tatgcttatg   1200
aaaggttatg taaataatcc agaagcaaca aaagaactta ttgacgaaga aggttggctg   1260
cacaccggag atattggata ttatgatgaa gaaaaacatt tctttattgt cgatcgtttg   1320
aagtctttaa tcaaatacaa aggataccaa gtaccacctg ccgaattaga atccgttctt   1380
ttgcaacatc catctatctt tgatgctggt gttgccggcg ttcctgatcc tgtagctggc   1440
gagcttccag gagccgttgt tgtactggaa agcggaaaaa atatgaccga aaagaagta   1500 atggattatg ttgcaagtca gtttcaaat gcaaaacgtt tacgtggtgg tgttcgtttt   1560
gtggatgaag tacctaaagg tcttactgga aaaattgacg gcagagcaat tagagaaatc   1620
cttaagaaac cagttgctaa gatg                                          1644
```

<210> SEQ ID NO 2
<211> LENGTH: 548
<212> TYPE: PRT
<213> ORGANISM: Luciola cruciata

<400> SEQUENCE: 2

Met Glu Asn Met Glu Asn Asp Glu Asn Ile Val Val Gly Pro Lys Pro
1               5                   10                  15

Phe Tyr Pro Ile Glu Glu Gly Ser Ala Gly Thr Gln Leu Arg Lys Tyr
                20                  25                  30

Met Glu Arg Tyr Ala Lys Leu Gly Ala Ile Ala Phe Thr Asn Ala Val
            35                  40                  45

Thr Gly Val Asp Tyr Ser Tyr Ala Glu Tyr Leu Glu Lys Ser Cys Cys
        50                  55                  60

Leu Gly Lys Ala Leu Gln Asn Tyr Gly Leu Val Val Asp Gly Arg Ile
65                  70                  75                  80

Ala Leu Cys Ser Glu Asn Cys Glu Glu Phe Phe Ile Pro Val Ile Ala
                85                  90                  95

```
Gly Leu Phe Ile Gly Val Gly Val Ala Pro Thr Asn Glu Ile Tyr Thr
                100                 105                 110

Leu Arg Glu Leu Val His Ser Leu Gly Ile Ser Lys Pro Thr Ile Val
            115                 120                 125

Phe Ser Ser Lys Lys Gly Leu Asp Lys Val Ile Thr Val Gln Lys Thr
        130                 135                 140

Val Thr Thr Ile Lys Thr Ile Val Ile Leu Asp Ser Lys Val Asp Tyr
145                 150                 155                 160

Arg Gly Tyr Gln Cys Leu Asp Thr Phe Ile Lys Arg Asn Thr Pro Pro
                165                 170                 175

Gly Phe Gln Ala Ser Ser Phe Lys Thr Val Glu Val Asp Arg Lys Glu
            180                 185                 190

Gln Val Ala Leu Ile Met Asn Ser Ser Gly Ser Thr Gly Leu Pro Lys
        195                 200                 205

Gly Val Gln Leu Thr His Glu Asn Thr Val Thr Arg Phe Ser His Ala
210                 215                 220

Arg Asp Pro Ile Tyr Gly Asn Gln Val Ser Pro Gly Thr Ala Val Leu
225                 230                 235                 240

Thr Val Val Pro Phe His His Gly Phe Gly Met Phe Thr Thr Leu Gly
                245                 250                 255

Tyr Leu Ile Cys Gly Phe Arg Val Val Met Leu Thr Lys Phe Asp Glu
            260                 265                 270

Glu Thr Phe Leu Lys Thr Leu Gln Asp Tyr Lys Cys Thr Ser Val Ile
        275                 280                 285

Leu Val Pro Thr Leu Phe Ala Ile Leu Asn Lys Ser Glu Leu Leu Asn
290                 295                 300

Lys Tyr Asp Leu Ser Asn Leu Val Glu Ile Ala Ser Gly Gly Ala Pro
305                 310                 315                 320

Leu Ser Lys Glu Val Gly Glu Ala Val Ala Arg Arg Phe Asn Leu Pro
                325                 330                 335

Gly Val Arg Gln Gly Tyr Gly Leu Thr Glu Thr Thr Ser Ala Ile Ile
            340                 345                 350

Ile Thr Pro Glu Gly Asp Asp Lys Pro Gly Ala Ser Gly Lys Val Val
        355                 360                 365

Pro Leu Phe Lys Ala Lys Val Ile Asp Leu Asp Thr Lys Lys Ser Leu
370                 375                 380

Gly Pro Asn Arg Arg Gly Glu Val Cys Val Lys Gly Pro Met Leu Met
385                 390                 395                 400

Lys Gly Tyr Val Asn Asn Pro Glu Ala Thr Lys Glu Leu Ile Asp Glu
                405                 410                 415

Glu Gly Trp Leu His Thr Gly Asp Ile Gly Tyr Tyr Asp Glu Glu Lys
            420                 425                 430

His Phe Phe Ile Val Asp Arg Leu Lys Ser Leu Ile Lys Tyr Lys Gly
        435                 440                 445

Tyr Gln Val Pro Pro Ala Glu Leu Glu Ser Val Leu Leu Gln His Pro
450                 455                 460

Ser Ile Phe Asp Ala Gly Val Ala Gly Val Pro Asp Pro Val Ala Gly
465                 470                 475                 480

Glu Leu Pro Gly Ala Val Val Val Leu Glu Ser Gly Lys Asn Met Thr
                485                 490                 495

Glu Lys Glu Val Met Asp Tyr Val Ala Ser Gln Val Ser Asn Ala Lys
            500                 505                 510

Arg Leu Arg Gly Gly Val Arg Phe Val Asp Glu Val Pro Lys Gly Leu
        515                 520                 525
```

Thr Gly Lys Ile Asp Gly Arg Ala Ile Arg Glu Ile Leu Lys Lys Pro
    530                 535                 540

Val Ala Lys Met
545

<210> SEQ ID NO 3
<211> LENGTH: 1644
<212> TYPE: DNA
<213> ORGANISM: Luciola cruciata

<400> SEQUENCE: 3

| | | | | | |
|---|---|---|---|---|---|
| atggaaaata | tggaaaacga | cgagaacatc | gtggtgggcc | ccaagccctt | ctaccccatc | 60 |
| gaggaaggca | gcgccggcac | ccagctgcgg | aagtacatgg | aaagatacgc | caagctgggc | 120 |
| gccattgcct | tcaccaacgc | cgtgaccggc | gtggactaca | gctacgccga | gtacctggaa | 180 |
| aagagctgct | gcctgggcaa | ggctctgcag | aactacggcc | tggtggtgga | cggccggatc | 240 |
| gccctgtgca | gcgagaactg | cgaggaattc | ttcatccccg | tgatcgccgg | cctgttcatc | 300 |
| ggcgtgggcg | tggctcccac | caacgagatc | tacacccctg | cgggagctgg | cacagcctg | 360 |
| ggcatcagca | agcccaccat | cgtgttcagc | agcaagaagg | gcctggacaa | agtcatcacc | 420 |
| gtgcagaaaa | ccgtgaccac | catcaagacc | atcgtgatcc | tggacagcaa | ggtggactac | 480 |
| cggggctacc | agtgcctgga | caccttcatc | aagcggaaca | cccccctgg | cttccaggcc | 540 |
| agcagcttca | gaccgtggag | gtggaccgg | aaagaacagg | tggccctgat | catgaacagc | 600 |
| agcggcagca | ccgcctgcc | caagggcgtg | cagctgaccc | acgagaacac | cgtgacccgg | 660 |
| ttcagccacg | ccagggaccc | catctacggc | aaccaggtgt | cccccggcac | cgccgtgctg | 720 |
| accgtggtgc | ccttccacca | cggcttcggc | atgttcacca | ccctgggcta | cctgatctgc | 780 |
| ggcttccggg | tggtgatgct | gaccaagttc | gacgaggaaa | ccttcctgaa | aaccctgcag | 840 |
| gactacaagt | gcacctacgt | gattctggtg | cccaccctgt | cgccatcct | gaacaagagc | 900 |
| gagctgctga | caagtacga | cctgagcaac | ctggtggaga | tcgccagcgg | cggagccccc | 960 |
| ctgagcaaag | aagtgggaga | ggccgtcgcc | aggcggttca | atctgcccgg | cgtgcggcag | 1020 |
| ggctacggcc | tgaccgagac | aaccagcgcc | atcatcatca | ccccgaggg | cgacgacaag | 1080 |
| cctggagcca | gcggcaaggt | ggtgcccctg | ttcaaggcca | agtgatcga | cctggacacc | 1140 |
| aagaagagcc | tgggccccaa | cagacggggc | gaagtgtgcg | tgaagggccc | catgctgatg | 1200 |
| aagggctacg | tgaacaaccc | cgaggccacc | aaagagctga | tcgacgaaga | gggctggctg | 1260 |
| cacaccggcg | acatcggcta | ctacgacgaa | gagaagcact | tcttcatcgt | ggaccggctg | 1320 |
| aagagcctga | tcaagtacaa | gggctatcag | gtgccccctg | ccgagctgga | aagcgtcctg | 1380 |
| ctgcagcacc | ccagcatctt | cgacgccggc | gtggccgggg | tgccagatcc | tgtggccggc | 1440 |
| gagctgcctg | cgccgtggt | ggtgctgaa | tccggcaaga | acatgaccga | aaagaagtg | 1500 |
| atggactacg | tcgccagcca | ggtgtccaac | gccaagcggc | tgagaggcgg | cgtgagattc | 1560 |
| gtggacgaag | tgccaaaggg | cctgaccggc | aagatcgacg | cagggccat | ccgggagatc | 1620 |
| ctgaagaaac | ccgtggccaa | gatg | | | | 1644 |

<210> SEQ ID NO 4
<211> LENGTH: 548
<212> TYPE: PRT
<213> ORGANISM: Luciola cruciata

<400> SEQUENCE: 4

Met Glu Asn Met Glu Asn Asp Glu Asn Ile Val Val Gly Pro Lys Pro

-continued

```
1               5                   10                  15
Phe Tyr Pro Ile Glu Glu Gly Ser Ala Gly Thr Gln Leu Arg Lys Tyr
            20                  25                  30

Met Glu Arg Tyr Ala Lys Leu Gly Ala Ile Ala Phe Thr Asn Ala Val
            35                  40                  45

Thr Gly Val Asp Tyr Ser Tyr Ala Glu Tyr Leu Glu Lys Ser Cys Cys
            50                  55                  60

Leu Gly Lys Ala Leu Gln Asn Tyr Gly Leu Val Val Asp Gly Arg Ile
65                      70                  75                  80

Ala Leu Cys Ser Glu Asn Cys Glu Glu Phe Phe Ile Pro Val Ile Ala
                85                  90                  95

Gly Leu Phe Ile Gly Val Gly Val Ala Pro Thr Asn Glu Ile Tyr Thr
                100                 105                 110

Leu Arg Glu Leu Val His Ser Leu Gly Ile Ser Lys Pro Thr Ile Val
                115                 120                 125

Phe Ser Ser Lys Lys Gly Leu Asp Lys Val Ile Thr Val Gln Lys Thr
            130                 135                 140

Val Thr Thr Ile Lys Thr Ile Val Ile Leu Asp Ser Lys Val Asp Tyr
145                     150                 155                 160

Arg Gly Tyr Gln Cys Leu Asp Thr Phe Ile Lys Arg Asn Thr Pro Pro
                165                 170                 175

Gly Phe Gln Ala Ser Ser Phe Lys Thr Val Glu Val Asp Arg Lys Glu
                180                 185                 190

Gln Val Ala Leu Ile Met Asn Ser Ser Gly Ser Thr Gly Leu Pro Lys
            195                 200                 205

Gly Val Gln Leu Thr His Glu Asn Thr Val Thr Arg Phe Ser His Ala
210                     215                 220

Arg Asp Pro Ile Tyr Gly Asn Gln Val Ser Pro Gly Thr Ala Val Leu
225                     230                 235                 240

Thr Val Val Pro Phe His His Gly Phe Gly Met Phe Thr Thr Leu Gly
                245                 250                 255

Tyr Leu Ile Cys Gly Phe Arg Val Val Met Leu Thr Lys Phe Asp Glu
                260                 265                 270

Glu Thr Phe Leu Lys Thr Leu Gln Asp Tyr Lys Cys Thr Tyr Val Ile
            275                 280                 285

Leu Val Pro Thr Leu Phe Ala Ile Leu Asn Lys Ser Glu Leu Leu Asn
            290                 295                 300

Lys Tyr Asp Leu Ser Asn Leu Val Glu Ile Ala Ser Gly Gly Ala Pro
305                     310                 315                 320

Leu Ser Lys Glu Val Gly Glu Ala Val Ala Arg Arg Phe Asn Leu Pro
                325                 330                 335

Gly Val Arg Gln Gly Tyr Gly Leu Thr Glu Thr Thr Ser Ala Ile Ile
                340                 345                 350

Ile Thr Pro Glu Gly Asp Asp Lys Pro Gly Ala Ser Gly Lys Val Val
            355                 360                 365

Pro Leu Phe Lys Ala Lys Val Ile Asp Leu Asp Thr Lys Lys Ser Leu
            370                 375                 380

Gly Pro Asn Arg Arg Gly Glu Val Cys Val Lys Gly Pro Met Leu Met
385                     390                 395                 400

Lys Gly Tyr Val Asn Asn Pro Glu Ala Thr Lys Glu Leu Ile Asp Glu
                405                 410                 415

Glu Gly Trp Leu His Thr Gly Asp Ile Gly Tyr Tyr Asp Glu Glu Lys
                420                 425                 430
```

```
His Phe Phe Ile Val Asp Arg Leu Lys Ser Leu Ile Lys Tyr Lys Gly
    435                 440                 445

Tyr Gln Val Pro Pro Ala Glu Leu Glu Ser Val Leu Leu Gln His Pro
    450                 455                 460

Ser Ile Phe Asp Ala Gly Val Ala Gly Val Pro Asp Pro Val Ala Gly
465                 470                 475                 480

Glu Leu Pro Gly Ala Val Val Leu Glu Ser Gly Lys Asn Met Thr
                485                 490                 495

Glu Lys Glu Val Met Asp Tyr Val Ala Ser Gln Val Ser Asn Ala Lys
            500                 505                 510

Arg Leu Arg Gly Gly Val Arg Phe Val Asp Glu Val Pro Lys Gly Leu
        515                 520                 525

Thr Gly Lys Ile Asp Gly Arg Ala Ile Arg Glu Ile Leu Lys Lys Pro
    530                 535                 540

Val Ala Lys Met
545

<210> SEQ ID NO 5
<211> LENGTH: 16
<212> TYPE: DNA
<213> ORGANISM: Luciola cruciata

<400> SEQUENCE: 5
accattgtta tactag                                                  16

<210> SEQ ID NO 6
<211> LENGTH: 16
<212> TYPE: DNA
<213> ORGANISM: Luciola cruciata

<400> SEQUENCE: 6
accatcgtga tcctgg                                                  16

<210> SEQ ID NO 7
<211> LENGTH: 16
<212> TYPE: DNA
<213> ORGANISM: Luciola cruciata

<400> SEQUENCE: 7
gatttgtcaa atttag                                                  16

<210> SEQ ID NO 8
<211> LENGTH: 16
<212> TYPE: DNA
<213> ORGANISM: Luciola cruciata

<400> SEQUENCE: 8
gacctgagca acctgg                                                  16

<210> SEQ ID NO 9
<211> LENGTH: 16
<212> TYPE: DNA
<213> ORGANISM: Luciola cruciata

<400> SEQUENCE: 9
gtcaaattta gttgag                                                  16

<210> SEQ ID NO 10
<211> LENGTH: 16
<212> TYPE: DNA
<213> ORGANISM: Luciola cruciata
```

```
<400> SEQUENCE: 10
gagcaacctg gtggag                                              16

<210> SEQ ID NO 11
<211> LENGTH: 16
<212> TYPE: DNA
<213> ORGANISM: Luciola cruciata

<400> SEQUENCE: 11
attgcatctg gcggag                                              16

<210> SEQ ID NO 12
<211> LENGTH: 16
<212> TYPE: DNA
<213> ORGANISM: Luciola cruciata

<400> SEQUENCE: 12
atcgccagcg gcggag                                              16

<210> SEQ ID NO 13
<211> LENGTH: 16
<212> TYPE: DNA
<213> ORGANISM: Luciola cruciata

<400> SEQUENCE: 13
ctttaggtcc taacag                                              16

<210> SEQ ID NO 14
<211> LENGTH: 15
<212> TYPE: DNA
<213> ORGANISM: Luciola cruciata

<400> SEQUENCE: 14
gccatcatca tcacc                                               15

<210> SEQ ID NO 15
<211> LENGTH: 16
<212> TYPE: DNA
<213> ORGANISM: Luciola cruciata

<400> SEQUENCE: 15
cctaacagac gtggag                                              16

<210> SEQ ID NO 16
<211> LENGTH: 16
<212> TYPE: DNA
<213> ORGANISM: Luciola cruciata

<400> SEQUENCE: 16 atcaccccg agggcg                                               16

<210> SEQ ID NO 17
<211> LENGTH: 16
<212> TYPE: DNA
<213> ORGANISM: Luciola cruciata

<400> SEQUENCE: 17
aacagacgtg gagaag                                              16

<210> SEQ ID NO 18
<211> LENGTH: 16
<212> TYPE: DNA
<213> ORGANISM: Luciola cruciata
```

-continued

```
<400> SEQUENCE: 18
aacagacggg gcgaag                                                      16

<210> SEQ ID NO 19
<211> LENGTH: 16
<212> TYPE: DNA
<213> ORGANISM: Luciola cruciata

<400> SEQUENCE: 19
gaagtttgtg ttaaag                                                      16

<210> SEQ ID NO 20
<211> LENGTH: 16
<212> TYPE: DNA
<213> ORGANISM: Luciola cruciata

<400> SEQUENCE: 20
cgacgacaag cctgga                                                      16

<210> SEQ ID NO 21
<211> LENGTH: 10
<212> TYPE: DNA
<213> ORGANISM: Luciola cruciata

<400> SEQUENCE: 21
aaactgtgaa                                                             10

<210> SEQ ID NO 22
<211> LENGTH: 10
<212> TYPE: DNA
<213> ORGANISM: Luciola cruciata

<400> SEQUENCE: 22
ttcacagttt                                                             10

<210> SEQ ID NO 23
<211> LENGTH: 10
<212> TYPE: DNA
<213> ORGANISM: Luciola cruciata

<400> SEQUENCE: 23
gaactgcgag                                                             10

<210> SEQ ID NO 24
<211> LENGTH: 10
<212> TYPE: DNA
<213> ORGANISM: Luciola cruciata

<400> SEQUENCE: 24
tgcacagcct                                                             10
```

MODIFIED *LUCIOLA CRUCIATA* LUCIFERASE GENE AND PROTEIN

CROSS REFERENCE TO RELATED APPLICATIONS

The present application is a Continuation-in-Part of U.S. Ser. No. 12/800,830 which issued as U.S. Pat. No. 8,206,961, which is Divisional of U.S. Ser. No. 12/287,561 which issued as U.S. Pat. No. 7,723,502.

FIELD OF THE INVENTION

The present invention relates to a novel codon optimized and stabilized luciferase gene (COS luciferase) derived from Japanese firefly *Luciola cruciata* luciferase. The invention further relates to production of a stabilized luciferase protein using such a modified gene and methods of analysis of cells using the luciferase gene and protein.

BACKGROUND OF THE INVENTION

Bioluminescence in certain organisms via the reaction of luciferin and luciferase is well known in the art. The use of the luciferase enzyme has become highly valuable as a genetic marker gene due to the convenience, sensitivity and linear range of the luminescence assay. Luciferase has been used in many experimental biological systems in both prokaryotic and eukaryotic cell culture, transgenic plants and animals, as well as cell-free expression systems.

For example, Japanese Firefly *Luciola cruciata* luciferase expression can be monitored as a genetic marker in cell extracts when mixed with substrates (D-luciferin, $Mg^{2+}$ ATP, and $O_2$), and the resulting luminescence measured using a luminescent detection device (containing a photomultiplier system or equivalent) such as luminometers or scintillation counters without the need of a reagent injection device. The *Luciola cruciata* luciferase activity can also be detected in living cells by adding D-luciferin or more membrane permeant analogs such as D-luciferin ethyl ester to the growth medium. This in vivo luminescence relies on the ability of D-luciferin or more membrane permeant analogs to diffuse through cellular and intracellular organelle membranes and on the intracellular availability of ATP and $O_2$ in these cells.

Despite its utility as a reporter, current luciferases isolated from various organisms, including insects and marine organisms are not necessarily optimized for expression or production in systems that are of most interest to the medical community and experimental molecular biologists. Accordingly, a need exists for a luciferase nucleic acid molecule that allows improved protein production in mammalian cells and tissues.

SUMMARY OF THE INVENTION

The present invention describes a novel codon optimized and stabilized luciferase gene coding for an improved luciferase protein. This new luciferase exhibits long-wavelength light emission, as well as improved thermostability and higher expression levels in mammalian cell systems, compared to native luciferase. Also described is a method of producing a stabilized luciferase protein by inserting a nucleic acid molecule of the present invention into an appropriate microorganism via a vector and culturing the microorganism to produce the stabilized luciferase protein.

BRIEF DESCRIPTION OF THE DRAWINGS

FIG. 1 shows a cleavage map of recombinant plasmid pDC57 DNA with endonuclease restriction enzymes.

FIG. 2 shows a cleavage map of recombinant plasmid pDC99 DNA with endonuclease restriction enzymes.

FIG. 3 shows a comparison of the native *L. cruciata* luciferase sequence with the codon optimized nucleotide sequence of the present invention.

FIG. 4. shows a comparison of Luciferase Expression Levels using the pDC99 vector of the present invention with the *Photinus pyralis* luciferase vector pSV40-GL3 in mammalian cells.

FIG. 5 shows a comparison of the thermal stability of the modified *Luciola cruciata* luciferase protein of the present invention with that of the *Photinus pyralis* wild type protein.

FIG. 6 shows use of the modified recombinant luciferase protein comprising the amino acid sequence SEQ ID NO:4 to quantitatively measure ATP concentration.

FIG. 7 shows the use of the modified recombinant luciferase protein comprising the amino acid sequence SEQ ID NO:4 to quantitatively measure the number of cells present in cell culture samples.

FIG. 8 shows the use of the modified recombinant luciferase protein comprising the amino acid sequence SEQ ID NO:4 to measure cell viability.

FIG. 9 shows the utility of the modified recombinant luciferase protein comprising the amino acid sequence SEQ ID NO:4 measuring cell cytotoxicity upon candidate drug treatment.

FIG. 10 shows that the modified recombinant luciferase protein comprising the amino acid sequence SEQ ID NO:4 can be used to measure a second enzyme in a coupled assay format.

DETAILED DESCRIPTION OF THE INVENTION

The wild-type sequence is known for the luciferase molecule from many different species and numerous modifications to those sequences have been described in the art. The present invention describes modifications to the nucleic acid molecule encoding luciferase in the Japanese firefly, *Luciola cruciata* as well as the luciferase protein itself. In a particular embodiment of the invention, the modified *Luciola cruciata* luciferase nucleic acid molecule encodes an improved luciferase enzyme which demonstrates greater thermostability (see FIG. 5 for an analysis of the thermal stability of the codon-optimized and stabilized *Luciola cruciata* luciferase protein of the present invention versus wild type protein at various temperatures) as well as a wavelength shift from green to red compared to native luciferase.

In another embodiment of the present invention, mRNA transcribed from the modified luciferase nucleic acid molecule is more stable in mammalian cells. This leads to enhanced levels of mRNA and results in greater expression of the luciferase (see FIG. 4 for a comparison of expression levels using the pDC99 vector of the present invention with the *Photinus pyralis* luciferase vector pSV40-GL3 in mammalian cells). In another embodiment, the level of mRNA is preferably increased by 10% to 200% over that seen when native sequence is expressed in mammalian cells.

In a particular embodiment of the present invention, the modified *Luciola cruciata* luciferase nucleic acid molecule is altered to remove RNAse cleavage motifs. The wild-type sequence shown in SEQ ID NO:1 has RNAse cleavage motifs at nucleotides 384-388, 682-686, and 929-933. In a preferred embodiment, the modified sequence is changed as shown in SEQ ID NO:3 and FIG. 3 to remove these motifs. In particular, nucleotides 384 to 388 are changed from (ATTTA) to GTTCA, nucleotides 682 to 686 are changed from (ATTTA) to ATCTA and nucleotides 929 to 933 are changed from ATTTA) to ACCTG.

Vectors such as retroviral vectors or other vectors intended for the introduction of recombinant DNA into mammalian cells will often contain active splice donor sequences. Instability is often created when a wild type gene from a non-mammal is carried by a retroviral vector due to the recognition of cryptic splice acceptor sequences in the wild type gene and splicing between these and splice donor sites present in the vector. In a particular embodiment of the present invention, cryptic splice acceptor sequences present in the wild type *L. cruciata* luciferase nucleic acid molecule are altered or removed.

In another particular embodiment of the present invention, cryptic splice acceptor sites found at bases 448 to 463, 919 to 934, 924 to 939, 940 to 955, 1148 to 1163, 1156 to 1171, 1159 to 1174, and 1171 to 1186 of the wild type sequence of SEQ ID NO:1 have one or more nucleotides altered.

In a particular embodiment, bases 448 to 463 of the wild type *L. cruciata* luciferase, i.e. ACCATTGTTATACTAG, herein SEQ ID NO:5 are changed in the COS luciferase to ACCATCGTGATCCTGG herein SEQ ID NO:6.

In another embodiment, bases 919 to 934 of the wild type *L. cruciata* luciferase, i.e. GATTTGTCAAATTTAG herein SEQ ID NO:7 are changed in the COS luciferase to GACCTGAGCAACCTGG herein SEQ ID NO:8.

In another embodiment, bases 924 to 939 of the wild type *L. cruciata* luciferase, i.e. GTCAAATTTAGTTGAG herein SEQ ID NO:9 are changed in the COS luciferase to GAGCAACCTGGTGGAG herein SEQ ID NO:10.

In another embodiment, bases 940 to 955 of the wild type *L. cruciata* luciferase, i.e. ATTGCATCTGGCGGAG herein SEQ ID NO:11 are changed in the COS luciferase to ATCGCCAGCGGCGGAG herein SEQ ID NO:12.

In another embodiment, bases 1148 to 1163 of the wild type *L. cruciata* luciferase, i.e. CTTTAGGTCCTAACAG herein SEQ ID NO:13 are changed in the COS luciferase to GCCATCATCATCACC herein SEQ ID NO:14.

In another embodiment, bases 1156 to 1171 of the wild type *L. cruciata* luciferase, i.e. CCTAACAGACGTGGAG herein SEQ ID NO:15 are changed in the COS luciferase to ATCACCCCGAGGGCG herein SEQ ID NO:16.

In another embodiment, bases 1159 to 1174 of the wild type *L. cruciata* luciferase, i.e. AACAGACGTGGAGAAG herein SEQ ID NO:17 are changed in the COS luciferase to AACAGACGGGGCGAAG herein SEQ ID NO:18.

In another embodiment, bases 1171 to 1186 of the wild type *L. cruciata* luciferase, i.e. GAAGTTTGTGTTAAAG herein SEQ ID NO:19 are changed in the COS luciferase to CGACGACAAGCCTGGA herein SEQ ID NO:20.

In a particular embodiment, the corresponding branchpoint sequences for the above cryptic splice sites in the wild type *L. cruciata* luciferase SEQ ID NO:1, are also altered to further suppress the splicing potential.

Palindromic sequences tend to have an adverse effect on translational efficiency and/or mRNA stability. The degree of these effects are generally directly related to the stability of the loop structures formed by these palindromic motifs. Accordingly, one embodiment of the present invention includes reducing the number of palindromic motifs. In a particular embodiment, palindromic motifs are altered by one or more nucleotides without altering the encoded luciferase enzyme activity and preferably without altering the amino acid sequence.

In a particular embodiment, a palindromic pair of motifs at bases 1087 to 1095 and 1218 to 1226 of the wild type *L. cruciata* luciferase, i.e. GCTTCTGGA and TCCAGAAGC, respectively are changed in the COS luciferase to GCCAGCGGC and CCCCGAGGC, respectively.

In a particular embodiment, a palindromic pair of motifs at bases 1151 to 1158 and 1185 to 1192 of the wild type *L. cruciata* luciferase, i.e. TAGGTCCT and AGGACCTA, respectively are changed in the COS luciferase to TGGGCCCC and GGGCCCCA, respectively.

In a particular embodiment, a palindromic pair of motifs at bases 255 to 264 and 350 to 359 of the wild type *L. cruciata* luciferase, ie. AAACTGTGAA and TTCACAGTTT, herein SEQ ID NO: 21 and SEQ ID NO:22 respectively are changed in the COS luciferase to GAACTGCGAG and TGCACAGCCT herein SEQ ID NO:23 and SEQ ID NO:24, respectively.

In a particular embodiment, a palindromic pair of motifs at bases 1381 to 1389 and 1508 to 1516 of the wild type *L. cruciata* luciferase, ie. TTGCAACAT and ATGTTGCAA, respectively are changed in the COS luciferase to CTGCAGCAC and ACGTCGCCA, respectively.

In a particular embodiment, a palindromic pair of motifs at bases 235 to 242 and 883 to 890 of the wild type *L. cruciata* luciferase, ie. AGAATTGC and GCAATTCT, respectively are changed in the COS luciferase to CGGATCGC and GCCATCCT, respectively.

In a particular embodiment, a palindromic pair of motifs at bases 445 to 452 and 740 to 747 of the wild type *L. cruciata* luciferase, ie. AAAACCAT and ATGGTTTT, respectively are changed in the COS luciferase to AAGACCAT and ACGGCTTC, respectively.

The wild type *Luciola cruciata* sequence incorporates several negatively cis-acting motifs that hamper expression in mammals are found in the wild-type sequence. In a particular embodiment of the present invention, the modified sequence contains no negative cis-acting sites (such as splice sites, poly(A) signals, etc.) which would negatively influence expression in mammalian cells.

The wild type *Luciola cruciata* sequence has a GC content that is quite low compared to mammalian sequences, which facilitates quick mRNA turnover. In another embodiment, the GC-content of the modified luciferase sequence is increased from about 37% to about 62%, prolonging mRNA half-life. Codon usage was adapted to the bias of *Homo sapiens* resulting in a high CM (codon adaptation index) value of 0.97, in comparison to 0.62 for the wild-type sequence. Accordingly, the optimized gene provides high and stable expression rates in *Homo sapiens* or other mammalian cell types.

The codon usage alterations generally lead to an increase the translation efficiency of the messenger RNA in a mammalian cell. It is a feature of the present invention that mRNA transcribed from the modified luciferase gene is more stably present in mammalian cells. This leads to enhanced levels of mRNA and results in greater expression of the luciferase protein. In a particular embodiment of the present invention, the level of mRNA is increased by 10% to 200% compared to expression of the native gene in the same cell. The codon optimization modifications are preferably incorporated such that resulting modified enzyme activity is not altered and most preferably that the amino acid sequence is not altered, except for desired changes described herein.

Many organisms display a bias for use of particular codons to code for addition of a specific amino acid in a growing peptide chain. Codon biases for differences in codon usage between organisms often correlate with the efficiency of translation of messenger RNA (mRNA), which in turn is believed to result from the properties of the codons being translated and the availability of particular transfer RNA (tRNA) molecules to be used in translation of the mRNA into protein. The predominance of selected tRNAs in a cell is generally a reflection of the codons used most frequently in peptide synthesis.

Codon usage in highly expressed mammalian genes are as follows:

[AminoAcid Codon Fraction] Gly GGG 0.15 Gly GGA 0.18 Gly GGT 0.21 Gly GGC 0.46 Glu GAG 0.68 Glu GAA 0.32 Asp GAT 0.38 Asp GAC 0.62 Val GTG 0.54 Val GTA 0.08 Val GTT 0.14 Val GTC 0.25 Ala GCG 0.14 Ala GCA 0.13 Ala GCT 0.29 Ala GCC 0.44 Arg AGG 0.14 Arg AGA 0.13 Ser AGT 0.10 Ser AGC 0.25 Lys AAG 0.75 Lys AAA 0.25 Asn AAT 0.26 Mn AAC 0.74 Met ATG 1.00 Ile ATA 0.06 Ile ATT 0.26 Ile ATC 0.67 Thr ACG 0.09 Thr ACA 0.18 Thr ACT 0.23 Thr ACC 0.50 Trp TGG 1.00 End TGA 0.30 Cys TGT 0.46 Cys TGC 0.54 End TAG 0.16 End TAA 0.53 Tyr TAT 0.35 Tyr TAC 0.65 Leu TTG 0.10 Leu TTA 0.03 Phe TTT 0.35 Phe TTC 0.65 Ser TCG 0.07 Ser TCA 0.08 Ser TCT 0.20 Ser TCC 0.31 Arg CGG 0.11 Arg CGA 0.05 Arg CGT 0.17 Arg CGC 0.40 Gln CAG 0.82 Gln CAA 0.18 His CAT 0.35 His CAC 0.65 Leu CTG 0.56 Leu CTA 0.05 Leu CTT 0.08 Leu CTC 0.18 Pro CCG 0.16 Pro CCA 0.19 Pro CCT 0.30 Pro CCC 0.35 The codon bias in the Gene is different to the highly expressed mammalian genes. Of the codons that potentially encode a particular amino some are very rarely used.

By the standard set forth in the preceding paragraph, the wild type *Luciola cruciata* sequence uses codons rarely used in mammalian systems with a high frequency. To have the most impact the most rarely used codons in highly expressed mammalian genes are preferably changed. In one embodiment of the present invention, at least about 90% of the rarely used codons found in the wild type sequence are altered to more preferred codons for the corresponding amino acid.

For example, the codon TTA is used to encode leucine in only 3% of cases in highly expressed mammalian systems, but is seen in the wild type luciferase of SEQ ID NO:1 at positions 87-89, 246-248, 339-341, 360-362, 405-407, 720-722, 774-776, 801-803, 828-830, 906-908, 933-935, 963-965, 1032-1034, 1152-1154, 1329-1331, 1368-1370, and 1542-1544. In one embodiment of the present invention, each of these positions is changed to CTG, which is a more commonly used in mammalian systems, thus optimizing the nucleic acid sequence for expression in mammals without changing the amino acid sequence. A preferred altered *Luciola cruciata* Luciferase gene is one where at least about 70%, 80%, 90%, 95%, 99% or 100% of codons are thus optimized for expression in a particular cell system. A specific embodiment of the present invention is the codon optimized and stabilized (COS) Luciferase set forth in SEQ ID NO:3

In another embodiment of the present invention, it is anticipated that conservative amino acid substitutions might be made throughout the enzyme without adversely altering the enzyme activity. One or more amino acid residues within the sequence can be substituted by another amino acid of a similar polarity, which acts as a functional equivalent, resulting in a silent alteration.

Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. Amino acids containing aromatic ring structures are phenylalanine, tryptophan, and tyrosine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

Particularly conservative amino acid substitutions are: (a) Lys for Arg or vice versa such that a positive charge may be maintained; (b) Glu for Asp or vice versa such that a negative charge may be maintained; (c) Ser for Thr or vice versa such that a free OH can be maintained; (d) Gln for Asn or vice versa such that a free $NH_2$ can be maintained; (e) Ile for Leu or for Val or vice versa as roughly equivalent hydrophobic amino acids; and (f) Phe for Tyr or vice versa as roughly equivalent aromatic amino acids. However it will be understood that less conservative substitutions may still be made without affecting the activity of the resulting luciferase enzyme.

In a particular embodiment of the present invention, the amino acid encoded at nucleotide position 875-877 in the wild-type sequence, SEQ ID NO:1 is changed from Ser(S) to Tyr(Y). This nucleic position corresponds with position 286 of the wild-type protein sequence, SEQ ID NO:2. This modification was found to have the surprising effect of making the resulting protein >100-fold more stable after 1 hour and >1000-fold more stable after 2 hours at 37° C. The modified luciferase also demonstrated greater thermostability than wild-type protein at room temperature. The substitution of Tyr for Ser at this position was also shown to have the surprising effect of shifting the emitted light from green to red (from 560 nm to 619 nm (pH 6)). The present invention also anticipates similar conservative amino acid substitutions at nucleotide position 875-877, including substituting Tyr, Lys, Leu, or Gln for Ser. These substitutions provide for a novel luciferase that can be useful in multiplexed assays along with a green emitting luciferase to monitor multiple activities. They also have significant application to tissue and in vivo analytical techniques, since mammalian tissues become more transparent at longer wavelengths (near and above about 620 nm).

It will be understood that the invention also encompasses a method of using the modified luciferase gene as a marker gene in live cells, wherein the nucleic acid molecules encoding the modified luciferase gene are provided in an expression vector with appropriate cis- and transacting expression elements and thereby provide cells expressing the modified luciferase gene that produce the modified enzyme intracellularly.

The modified luciferase of the present invention might be incorporated as part of a fusion protein. Additionally the invention encompasses a cloning vehicle having a sequence encoding the modified luciferase gene.

The luciferase gene will typically be positioned operably linked to a promoter. Preferably the promoter is a mammalian promoter, and may be selected from one of the many known mammalian promoters. In the context of this invention the term luciferase gene refers to the open reading frame encoding the modified luciferase protein.

The levels of expression of the luciferase gene will be proportional to the activity of the promoter used in the expression vector. The present invention describes methods of measuring promoter activity based upon the levels of luciferase protein produced by specific luciferase gene—promoter constructs.

Additionally other nucleotide motifs might be introduced to enhance transcription and/or translation such as a Kozak consensus sequence or transcriptional enhancers or transcription factors.

The present invention describes methods for analysis of transcriptional enhancer or transcription factor levels in a cell sample by measurement of luciferase protein production in a cell line that has been transfected with a specific luciferase gene—promoter construct.

The present invention describes a plasmid vector for expression in mammalian cells, a bacterial vector for expression in plant cells, but also contemplates a retroviral vector or a lentiviral vector, that includes the modified luciferase gene, or a cell carrying the modified luciferase gene.

The present invention also describes methods for isolating the modified recombinant luciferase protein comprising the amino acid sequence SEQ ID NO:4 from *E. coil* bacterial culture. It is understood that the protein may be expressed in and purified from other cell types, including but not limited to mammalian cells, plant cells, yeast, fungi or in other bacterial cell types. These methods of overproduction of the purified or partially purified protein useful for analytical assays of the present invention will be obvious to a person skilled in the art.

The present invention also describes methods for use of the modified recombinant luciferase protein in analytical assays. Natural and recombinant luciferase enzymes have been utilized as a method of detecting minute concentrations of ATP using the luciferin-luciferase assay. As low as $10^{-16}$ moles of ATP has been detected with the enzyme from *Photinus pyralis*. And the luciferase reaction is highly specific for ATP. Other nucleoside triphosphates or ATP analogs are not usable substrates for the enzyme. The luciferin-luciferase assay conditions include D-luciferin, molecular oxygen, magnesium ion, the cofactor coenzyme A, dithiothreitol, bovine serum albumin in a buffer, typically 50 mM tricine or 25 mM glycylglycine, at pH 7.8. A commercially available kit containing both the reaction buffer (25 mM Glycylglycine, 15 mM MgSO4, 4 mM EDTA, 15 mM Potassium phosphate pH 7.8, 1 mM DTT, and 1 mM Coenzyme A) as well as a cell lysis buffer for use in cell assays (25 mM Tris-phosphate (pH 7.8) containing 10% glycerol, 1% Triton X-100, 1 mg/ml BSA, 2 mM EGTA and 2 mM DTT.) can be used for this purpose.

The ability to measure the concentration of ATP present in samples has allowed the luciferin-luciferase assay to become a widely used biochemical reporter for cell metabolic activity or for the specific activity of a variety of other enzymes. In general, the increase or decrease in ATP concentration has been well documented for use as a sensitive measure of enzyme activity for kinases, phosphotransferases, phosphatases, in immunoassays such as enzyme-linked immunoadsorbent (ELISA) assays, in cell viability assays where total ATP present in a cell sample is measured, in cytotoxicity assays wherein the levels of ATP produced by a cell sample is either increased or decreased with the addition of a chemical agent or to simply measure the number of cells present in a cell sample by measurement of total ATP. Examples of these assays are given below.

The present invention also includes measuring the levels of a second enzyme using the modified recombinant luciferase protein by use of alternate luciferin-based analogs. In this manner, the luciferin-luciferase assay has been used for measurement of protease, peptidase, phosphatase, sulfatase, dealkylase and glycosidase enzymes. Assay methods have been demonstrated and are well known to one skilled in the art. Amino acid, peptide or protein conjugates of 6-amino-D-luciferin at either the 6-amino position (for amino-peptidases) or at the 4-carboxy position (for carboxypeptidases) have been prepared and utilized in peptidase or protease assays.

The substrate D-Luciferin 6-O-phosphate is a sensitive substrate for coupled analysis of alkaline phosphatase, acid phosphatase and protein phosphatases. Upon phosphatase activity, D-luciferin is produced whose levels are detected using the luciferin-luciferase assay. The levels of phophatase activity can therefore be related to light output, when excess luciferase is present in the luciferin-luciferase assay. In a similar manner, D-luciferin-6-O-sulfate has been used to monitor the levels of arylsulfatase.

The substrate D-Luciferin-6-O-β-D-galactopyranoside (D-Luciferin-6-O-β-D-galactoside) is a sensitive substrate for detection of beta-galactosidase enzyme activity. This analog of D-Luciferin contains a β-galactoside attached at the 6-O-position, and thus is not a substrate for the firefly luciferase enzyme until the galactose is removed by β-galactosidase activity. As such it represents an ultrasensitive substrate for chemiluminescent measurement of galactosidase activity in homogeneous assays, or in cell lysate samples when excess luciferase is present in the luciferin-luciferase assay. The levels of β-galactosidase activity can therefore be related to light output, when excess luciferase is present in the luciferin-luciferase assay. Similar conjugation of other sugars or oligosaccharides at the 6-O-position of D-luciferin can be used to measure the levels of other specific glycosidase enzymes.

Cytochrome P450 assays employ a 6-O-methyl or 6-O-benzyl ether analog of D-luciferin as substrate. Upon cytochrome P450 activity, these 6-O-ether substituents are removed from the substrate, allowing the free D-luciferin to act in turn as a substrate for the luciferin-luciferase assay. The levels of CP450 are therefore related to the light output, when excess luciferase is present in the luciferin-luciferase assay.

Finally monoamine oxidase assays employ a derivative of beetle luciferin ((4S)-4,5-dihydro-2-(6-hydroxybenzothiazolyl)-4-thiazolecarboxylic acid). Monoamine oxidase activity converts this luciferin derivative to luciferin methyl ester, which is quickly converted to D-luciferin by intracellular esterases, or by added esterase to homogeneous assays. The levels of monoamine oxidase are therefore related to the light output, when excess luciferase is present in the luciferin-luciferase assay.

In addition, using an antibody-linked enzyme for analysis of these enzymes can be employed to detect specific ligands, epitopes or structures in biological samples by coupling the linked enzyme activity with the luciferin-luciferase assay in the aforementioned luciferase protein coupled assay. Examples of these coupled assays are given below. Other coupled assays or methods will be obvious to a person skilled in the art.

The examples below are given so as to illustrate the practice of this invention. They are not intended to limit or define the entire scope of this invention.

EXAMPLES

Example 1

Construction of the Modified *Luciola cruciata* Luciferase Gene

The synthetic COS luciferase gene, SEQ ID NO:3, was assembled from synthetic oligonucleotides and/or PCR products. The fragment was cloned into pMK (kanR) using KpnI and SacI restriction sites. The plasmid DNA was purified (PureYield™ Plasmid Midiprep, Promega) from transformed bacteria and concentration determined by UV spectroscopy. The final construct was verified by sequencing. The sequence congruence within the used restriction sites was 100%.

Example 2

Subcloning of the Modified *Luciola cruciata* Luciferase Gene into the pCMV and pSV40 Vectors The synthetic COS luciferase assembled in Example 1 was excised from pMK cloning vector using flanking XhoI and NotI restriction enzymes (Fast Digest, Fermentas). The excised fragment was gel-purified (GenElute Gel Extraction Kit, Sigma) and quantitated using MassRuler™ DNA Ladder Mix (Fermentas). The excised gene was subcloned into both pCMV and pSV40 Mammalian Expression Vectors using corresponding XhoI and NotI restriction sites. The completed pCMV construct was named pDC57. The completed pSV40 construct was named pDC99.

Example 3

Subcloning of the Modified *Luciola cruciata* Luciferase Gene into the pNosdc Binary Vector for Expression in Plants The synthetic COS luciferase assembled in Example 1 was amplified using the Polymerase Chain reaction. Amplification was performed with primers including XmaI and SacI restriction sites. The ends of the amplified fragment were cut with XmaI and SacI restriction enzymes (New England Biolabs) and the fragment was gel-purified (GenElute Gel Extraction Kit, Sigma) and quantitated using MassRuler™ DNA Ladder Mix (Fermentas). The amplified fragment was subcloned into the pNosdc binary vector for transformation of plants via *Agrobacterium tumefaciens*. The completed construct was named pNosdcCOS.

Example 4

Transfection of Mammalian Cells with the Modified *Luciola cruciata* Luciferase Vectors pDC57 and pDC99

NIH 3T3 cells (murine tumor fibroblasts) were grown to 80% confluence in 100 mm tissue culture plates. Cells were transfected with either pDC57 or pDC99 using Lipofectamine and PLUS reagents (Invitrogen).

Example 5

Analysis of Luciferase Expression Levels Using the pDC99 Vector and Comparison to the Luciferase Expression Using the *Photinus pyralis* Luciferase Vector pSV40-GL3 in Mammalian Cells Transfected NIH 3T3 cells prepared in Example 4 were lysed using a lysis buffer comprised of 25 mM Tris-phosphate (pH 7.8), containing 10% glycerol, 1% Triton X-100, 1 mg/ml BSA, 2 mM EGTA and 2 mM DTT. Cells were washed with 1× Phosphate Buffered Saline, and lysis buffer (1 mL) was added to surface of plate. Plate was incubated for 30 mins, and lysate was collected. Additionally, NIH 3T3 cells were transfected with pSV40-GL3, a construct containing wild type luciferase from *Photinus pyralis*, as per the method in Example 4 and lysed using the above method. As a negative control, untransfected NIH 3T3 cells were also lysed by the above method.

Cell lysates were diluted using lysis buffer, and added in triplicate to wells of a solid white 96-well plate (Costar). Added to cell lysates was a reagent containing 1 mM D-luciferin and 2 mM ATP in a buffer comprised of 25 mM Glycylglycine, 15 mM MgSO4, 4 mM EDTA, 15 mM Potassium phosphate pH 7.8, 1 mM DTT, and 1 mM Coenzyme A.

Luminescence was recorded using a Perkin-Elmer HTS7000 Plus Bio Assay Reader (200 ms integration time). Results of these analyses are shown in FIG. 4.

Example 6

Analysis of the Thermal Stability of the Modified *Luciola cruciata* Luciferase Protein Versus Wild Type Protein Cell lysates from NIH 3T3 cells transfected with pDC99 and pSV40-GL3 (transfected according to method in Example 4), as well as untransfected cells were prepared as described in Example 5a. Luminescence of each sample was recorded as described in Example 5a to obtain a baseline value of enzyme activity. Portions of each sample were then incubated in water baths at 37° C., 42° C., and 55° C. A portion of each sample was also incubated at ambient room temperature (25° C.). At 1 hour and 2 hour intervals, aliquots of each temperature-incubation were removed and assayed for activity using the method described in Example 5a. Results of these analyses are shown in FIG. 5.

Example 7

Isolation of the Modified *Luciola cruciata* Luciferase Protein from Bacterial Culture An expression vector containing the codon optimized and stabilized luciferase gene (COS) was constructed by inserting a XhoI/BamHI fragment from M1395 or similar plasmid into Histidine tag expression vector pET-His (modified from pET-3a, ATCC #87036). *Escherichia coli* strain BL21(DE3)pLysS harboring this expression vector was grown to an OD600 of 0.6 by incubation at 37° C. with vigorous shaking in 500 mL LB Broth containing the appropriate selection antibiotic (ampicillin 100 μg/ml and chloramphenicol 35 μg/ml). Then this culture was induced for expression with 0.4 mM IPTG at 16° C. overnight. Bacterial cells were pelleted by centrifugation at 5,000×g, and the pellet resuspended in a bacterial cell lysis buffer containing 25 mM Tris-HCl (pH7.8), 100 mM NaCl, 10% glycerol, 1% TritonX-100 supplemented with freshly added 1 mM DTT, 0.25 mM AEBSF and 5 μg/ml aprotinin. The suspension was sonicated four times for 1 minute and centrifuged at 15,000 g to retrieve a Triton soluble fraction. This Triton soluble supernatant was adjusted to contain 300 mM NaCl and 10 mM imidazole and then applied onto Ni sepharose column pre-equilibrated with binding buffer containing 25 mM Tris-HCl (pH7.8), 300 mM NaCl and 10 mM imidazole. The column was washed with binding buffer and eluted with a buffered solution containing 25 mM Tris-HCl (pH7.8), 300 mM NaCl and 250 mM imidazole. Each of the eluted fractions were assayed for luciferase activity and applied to SDS-PAGE to assess the purity. The elutes that contain active luciferase were pooled and dialyzed against 25 mM Tris-HCl (pH7.8), 150 mM NaCl and 0.5 mM EDTA.

Luciferase activity assay was performed in reaction buffer (25 mM Glycylglycine, 15 mM MgSO4, 4 mM EDTA, 15 mM Potassium phosphate pH 7.8, 1 mM DTT, and 1 mM Coenzyme A) followed by addition of a reagent containing 1 mM D-luciferin and 2 mM ATP to start the reaction. Luminescence was recorded after 5 minutes using a BioTek Synergy Mx microplate reader with gain setting of 135.

Example 8

Transfection of Plants with Codon Optimized and Stabilized Luciferase (COS)

*Agrobacterium tumefaciens* are transfected with pdc-NosCOS according to freeze-thaw protocol previously described (D. Weigel, J. Glazerbrook, pp. 125-126 (2002)). *Arabidopsis thaliana* (strain CS-20) are transfected by the floral dip method using the aforementioned transfected *Agrobacterium*, using the protocol described previously (D. Weigel, J. Glazerbrook, pp. 129-130 (2002)). Seedlings are selected on Murashige and Skoog Agar plates containing 50 µg/mL kanamycin, as described previously (D. Weigel, J. Glazerbrook, pp. 131-132 (2002)).

Protein is extracted from plant tissue according to the following procedure. Tissue is lyophilized and ground into a fine powder in a mortar. The powder is placed in a microcentrifuge tube and suspended in reaction buffer (25 mM Glycylglycine, 15 mM MgSO4, 4 mM EDTA, 15 mM Potassium phosphate pH 7.8, 1 mM DTT, and 1 mM Coenzyme A) by vortexing. The tube is incubated at 10 mins at room temperature to solubilize proteins, followed by centrifugation at >15,000×g to pellet solid material. The supernatant is transferred to a fresh tube, and added in triplicate to wells of a solid white 96-well plate (Costar). Added to tissue extracts is a reagent containing 1 mM D-luciferin and 2 mM ATP in a buffer comprised of 25 mM Glycylglycine, 15 mM MgSO4, 4 mM EDTA, 15 mM Potassium phosphate pH 7.8, 1 mM DTT, and 1 mM Coenzyme A.

Luminescence is recorded using a Perkin-Elmer HTS7000 Plus Bio Assay Reader (200 ms integration time).

Example 9

Measurement of ATP Concentration

A titration series of ATP samples in concentrations ranging from 10 µM to 2 mM was prepared in Reaction buffer (25 mM Glycylglycine, 15 mM MgSO4, 4 mM EDTA, 15 mM Potassium phosphate pH 7.8, 1 mM DTT, and 1 mM Coenzyme A) containing D-Luciferin (1 mM). A concentration of 1 mM D-Luciferin was kept consistent in all titrations. 50 µl of the above-mentioned titration series samples were mixed with 4 µg of the modified recombinant luciferase protein SEQ ID NO:4 (COS) in 50 µl protein stabilizing buffer and luminescence was immediately recorded with Biotek Synergy Mx microplate reader under gain setting of 135 and integration time of 1 second. Representative data shown in FIG. 6 shows that the modified recombinant luciferase protein can be used to quantitatively measure ATP concentration.

Example 10

Measurement of Cell Number

MDA-MB-231T human breast carcinoma cells were seeded ranging from 37 to 20000 cells per well into 96-well microplates and incubated overnight. The next day, plates containing the cells were washed with PBS once and lysis buffer (25 mM Tris-phosphate pH7.8, 10% glycerol, 1% Triton X-100, 1 mg/ml BSA, 2 mM EGTA and 2 mM DTT) was added (60 µl per well). The cell plates were placed on ice for 30 minutes to ensure complete lysis. 50 µl of the lysate from each well was incubated with 50 µl of luciferin/luciferase mixture containing 10 µl of the modified recombinant luciferase protein SEQ ID NO:4 (COS) and 1 mM D-Luciferin in reaction buffer (25 mM Glycylglycine, 15 mM MgSO4, 4 mM EDTA, 15 mM Potassium phosphate pH 7.8, 1 mM DTT, and 1 mM Coenzyme A). Luminescence was immediately recorded with Biotek Synergy Mx microplate reader under gain setting of 135 and integration time of 1 second. Representative data in FIG. 7 shows that the modified recombinant luciferase protein can be used to quantitatively measure the number of cells present in culture samples.

Example 11

Measurement of Cell Viability

MDA-MB-231T human breast carcinoma cells were seeded at 7000 cells per well using 100 µl RPMI1640 complete medium with 9% FCS in 96-well plate and incubated overnight. After 24 hours, a series of dilutions of doxorubicin in complete medium were prepared from 0.1 to 10 µM. 100 µl of each of these doxorubicin solution were added to triplicate wells in the cell plate, giving a final concentration of doxorubicin half of that titrated in the test wells. The cell plate was allowed to incubate at 37° C., and 5% $CO_2$ for additional 48 hrs. The cell plate was then observed under microscope and percentage of surviving cells was recorded by comparing to vehicle-treated wells. After microscopic evaluation, the cell plate was washed with PBS once. 60 µl of lysis buffer (25 mM Tris-phosphate pH7.8, 10% glycerol, 1% Triton X-100, 1 mg/ml BSA, 2 mM EGTA and 2 mM DTT) was added per well and plate was placed on ice for 30 minutes to ensure complete cell lysis. Next, 50 µl of the lysate was mixed with equal volume of luciferin/luciferase solution which contains 4 ug of the modified recombinant luciferase protein SEQ ID NO:4 (COS) and 1 mM D-Luciferin in reaction buffer (25 mM Glycylglycine, 15 mM MgSO4, 4 mM EDTA, 15 mM Potassium phosphate pH 7.8, 1 mM DTT, and 1 mM Coenzyme A). Luminescence was immediately recorded with Biotek Synergy Mx microplate reader under a gain setting of 135 and integration time of 1 second. Representative data for the levels of drug cytotoxicity are shown in FIG. 8, indicating that the modified recombinant luciferase protein can be used to measure cell viability. These data were in accord with the visual analysis of the cells obtained prior to luciferase-luciferin reaction.

Example 12

Cellular Cytotoxicity Measurements

MDA-MB-231T human breast carcinoma cells were seeded at 10000 cells per well with 100 µl complete medium in 96-well plate and incubated overnight. After 24 hours a series of dilutions of doxorubicin were prepared in complete medium from 0.1 to 10 µM. 100 µl of each doxorubicin solution were added to each well in cell plate, giving a final concentration of doxorubicin at half of the titrated amounts. The cell plates were incubated at 37° C. in a 5% $CO_2$ incubator for additional 24 hrs. The cell plate was then observed under microscope and percentage of surviving cells was recorded by comparing to vehicle-treated wells. Afterwards, the cell plate was washed with PBS once. 60 µl of lysis buffer (25 mM Tris-phosphate pH7.8, 10% glycerol, 1% Triton X-100, 1 mg/ml BSA, 2 mM EGTA and 2 mM DTT) was added per well and plate was placed on ice for 30 minutes to ensure complete cell lysis. 50 µl of the lysate was mixed with equal volume of luciferin/luciferase solution which contains 4 ug of the modified recombinant luciferase protein comprising the amino acid sequence SEQ ID NO:4 (COS) and 1 mM D-Luciferin in reaction buffer (25 mM Glycylglycine, 15 mM MgSO4, 4 mM EDTA, 15 mM Potassium phosphate pH 7.8, 1 mM DTT, and 1 mM Coenzyme A). Luminescence was immediately recorded with Biotek Synergy Mx microplate reader under gain setting of 135 and integration time of 1 second. Representative data found in FIG. 9 shows that the modified recombinant luciferase protein can be used to measure cell cytotoxicity upon drug treatment.

Example 13

Carboxypeptidase Assay

A sample containing 750 uL Tris buffer (50 mM Tris-HCl, 20 mM $CaCl_2$, pH 8.0) and 50 uL of the substrate solution (1.0 mmol D-Luciferyl-L-Phenylalanine in $H_2O$) is incubated for 5 min at 25° C. and then 300 uL of various concentrations of test Carboxypeptidase A samples (20 uL samples of enzyme serial dilutions from 0-40 u/mL in 0.001 M HCl) are added. After 60 min. a 100 uL sample of these reaction solutions are removed and added to 100 uL of a luciferin-luciferase cocktail containing the modified recombinant luciferase protein SEQ ID NO:4 (4 ug) in 25 mM Glycylglycine, 15 mM $MgSO_4$, 4 mM EDTA, 15 mM Potassium phosphate pH 7.8, 1 mM DTT, and 1 mM Coenzyme A.

The levels of Carboxypeptidase A in the test samples are determined by immediately measuring the light output using a BioTek Synergy Mx microplate reader using the luminescence mode with integration for 60 sec. Integrated light emission is proportional to the Carboxypeptidase A enzyme levels of the test samples. It is possible to determine with this test an amount of Carboxypeptidase A down to 10 pg.

Example 14

Aminopeptidase Assay of Trypsin and Trypsin-Like Activity

Measurement of levels of the aminopeptidase enzyme trypsin is performed using the substrate N-α-acetyl-L-arginyl-amino-luciferin, as follows. A sample containing 750 uL Tris buffer (50 mM Tris-HCl, 20 mM $CaCl_2$, pH 8.0) and 50 uL of the substrate solution (1.0 mmol N-α acetyl-L-arginyl-amino-luciferin in $H_2O$) is incubated for 5 min at 25° C. and then 300 uL of various concentrations of test trypsin samples (20 uL samples of enzyme serial dilutions from 0-40 u/mL in 0.001 M HCl) are added. After 20 min. a 100 uL sample of these reaction solutions are removed and added to 100 uL of a luciferin-luciferase cocktail containing the modified recombinant luciferase protein SEQ ID NO:4 (4 ug) in 25 mM Glycylglycine, 15 mM $MgSO_4$, 4 mM EDTA, 15 mM Potassium phosphate pH 7.8, 1 mM DTT, and 1 mM Coenzyme A.

The levels of trypsin in the test samples are determined by immediately measuring the light output using a BioTek Synergy Mx microplate reader using the luminescence mode with integration for 60 sec. Integrated light emission is proportional to the trypsin enzyme levels of the test samples. It is possible to determine with this test an amount of trypsin down to 10 fg. N-α-acetyl-L-lysyl-aminoluciferin may also be used as an equivalent substrate for tyrpsin determinations. This test can also be used for determining kallikrein.

Example 15

β-Galactosidase Assay

Solutions containing 0.16-100 μM of D-luciferin-6-O-β-D-galactopyranoside (MGT Product M1087) were incubated with saturating amounts of β-galactosidase (0.05 U) in 50 μl of reaction buffer (PBS with 2 mM $MgSO_4$) in 96-well microplates. The reaction was allowed proceed at room temperature for 30 minutes. Then this reaction was mixed with ATP/luciferase solution (50 uL) containing 2 mM ATP and 4 μg of the modified recombinant luciferase protein SEQ ID NO:4 (COS) in reaction buffer (25 mM Glycylglycine, 15 mM MgSO4, 4 mM EDTA, 15 mM Potassium phosphate pH 7.8, 1 mM DTT, and 1 mM Coenzyme A). Luminescence was immediately recorded with Biotek Synergy Mx microplate reader under gain setting of 135 and integration time of 5 seconds (full spectrum emission). Representative data shown in FIG. 10 shows that the modified recombinant luciferase protein can be used to measure a second enzyme, β-galactosidase, in a coupled assay format.

Example 16

Phosphatase Assay

Solutions containing 0.10-100 uM of D-luciferin-6-O-phosphate were incubated with saturating amounts of alkaline phosphate (0.05 U) in 50 ul of reaction buffer (PBS with 2 mM $MgSO_4$) in 96-well microplates. The reaction was allowed proceed at room temperature for 60 minutes. Then this reaction was mixed with ATP/luciferase solution (50 uL) containing 2 mM ATP and 4 ug of the modified recombinant luciferase protein SEQ ID NO:4 (COS) in reaction buffer (25 mM Glycylglycine, 15 mM MgSO4, 4 mM EDTA, 15 mM Potassium phosphate pH 7.8, 1 mM DTT, and 1 mM Coenzyme A). Luminescence was immediately recorded with Biotek Synergy microplate reader under gain setting of 135 and integration time of 5 seconds. The levels of light emission were proportional to alkaline phosphatase concentration in each case.

Example 17

Aryl Sulfatase Assay

Solutions containing 0.10-100 uM of D-luciferin-6-O-sulfate were incubated with saturating amounts of aryl sulfatase (0.05 U) in 50 ul of reaction buffer (PBS with 2 mM $MgSO_4$) in 96-well microplates. The reaction was allowed proceed at room temperature for 60 minutes. Then this reaction was mixed with ATP/luciferase solution (50 uL) containing 2 mM ATP and 4 ug of the modified recombinant luciferase protein comprising the amino acid sequence SEQ ID NO:4 (COS) in reaction buffer (25 mM Glycylglycine, 15 mM MgSO4, 4 mM EDTA, 15 mM Potassium phosphate pH 7.8, 1 mM DTT, and 1 mM Coenzyme A). Luminescence was immediately recorded with Biotek Synergy microplate reader under gain setting of 135 and integration time of 5 seconds. The levels of light emission were proportional to aryl sulfatase concentration in each case.

Example 18

Cytochrome P450 Assay

Solutions containing 1.0-100 uM of D-luciferin-6-O-methyl ether (MGT Product M0236) were incubated with saturating amounts of cytochrome P450 enzyme (0.5 U) in 50 ul of reaction buffer (PBS with 2 mM $MgSO_4$) in 96-well microplates. The reaction was allowed proceed at room temperature for 90 minutes. Then this reaction was mixed with ATP/luciferase solution (50 uL) containing 2 mM ATP and 4 ug of the modified recombinant luciferase protein comprising the amino acid sequence SEQ ID NO:4 (COS) in reaction buffer (25 mM Glycylglycine, 15 mM MgSO4, 4 mM EDTA, 15 mM Potassium phosphate pH 7.8, 1 mM DTT, and 1 mM Coenzyme A). Luminescence was immediately recorded with Biotek Synergy microplate reader under gain setting of 135 and integration time of 5 seconds. The levels of light emission were proportional to cytochrome P450 enzyme concentration in each case.

Example 19

Transcription Factor Level Analysis

Promoter Activity Assay

An IRF-3/pDC99 (COS) luc expression vector for IRF-3, was constructed as follows. Mouse IRF-3 cDNA was obtained by RT-PCR of the total RNA from mouse embryonic fibroblasts, cloned into the pCRII (Stratagene) vector (pIRF-3), and the nucleotide sequence of the cDNA was confirmed. Sense and antisense primers flanking the IRF3 gene and incorporating restrictions sites were used for RT-PCR. The cDNA was excised by NotI and XbaI digestion and cloned into the NotI and XbaI sites of pDC99 vector. The sequence of the linker DNA was confirmed by restriction digest and oligonucleotide sequencing. After transfection into NIH/3T3 cells cultured in Dulbecco's modified Eagle's medium supplemented with 9% FCS, using LipofectAmine reagent (GibcoBRL), the cells were grown in culture for 3 days at 37° C. and 5% $CO_2$ atmosphere. Some plates of cells were infected with the Newcastle disease virus (NDV), and allowed to continue growth overnight. The next day, plates containing both infected and control cells were washed with PBS once and lysis buffer (25 mM Tris-phosphate pH7.8, 10% glycerol, 1% Triton X-100, 1 mg/ml BSA, 2 mM EGTA and 2 mM DTT) was added (60 µl per well). The cell plates were placed on ice for 30 minutes to ensure complete lysis. 50 µl of the lysate from each well was incubated with 50 µl of luciferin/luciferase mixture containing 10 ug the modified recombinant luciferase protein SEQ ID NO:4 (COS) and 1 mM D-Luciferin in reaction buffer (25 mM Glycylglycine, 15 mM MgSO4, 4 mM EDTA, 15 mM Potassium phosphate pH 7.8, 1 mM DTT, and 1 mM Coenzyme A). Luminescence was immediately recorded with Biotek Synergy Mx microplate reader under gain setting of 135 and integration time of 1 second. Cells infected with the NDV virus exhibited increased luminescence indicating transcription factor upregulation of the luciferase gene. This assay indicated that the observed luminescence was the result of differing promoter activities in transient transfections of the cells grown in culture.

Example 20

ELISA Assay

Alkaline Phosphatase Linked Antibody Assay

Human T cells were grown to 5×10(4) cells per well in 12-well tissue culture plates, washed and contacted with mouse monoclonal antibodies to cell surface hepatitis B surface antigen (HBsAg). The cells were washed with PBS and treated with a 1/1000 dilution of an anti-mouse IgG-alkaline phosphatase conjugate. After a second Wash step with PBS, a solution containing 100 uM of D-luciferin-6-O-phosphate was added and incubated in 250 ul of reaction buffer (PBS with 2 mM $MgSO_4$) in 96-well microplates at room temperature for 60 minutes. Then this reaction was mixed with ATP/luciferase solution (50 uL) containing 2 mM ATP and 4 ug of the modified recombinant luciferase protein SEQ ID NO:4 (COS) in reaction buffer (25 mM Glycylglycine, 15 mM MgSO4, 4 mM EDTA, 15 mM Potassium phosphate pH 7.8, 1 mM DTT, and 1 mM Coenzyme A). Luminescence was immediately recorded with Biotek Synergy microplate reader under gain setting of 135 and integration time of 5 seconds. The levels of light emission were proportional to the hepatitis B surface antigen (HBsAg) levels in each case.

Example 21

Measurement of Kinase Enzyme Activity

Protein kinase assay buffer (40 mM Tris pH7.4, 20 mM Magnesium acetate) containing 5 µM Kemptide substrate, 1 µM ATP and 0.005-5.00 units of protein Kinase A (PKA) was incubated at room temperature for 30 minutes. 50 µl of the above reaction was mixed with equal volume of luciferin/luciferase solution which contains 4 ug of the modified recombinant luciferase protein SEQ ID NO:4 (COS) and 1 mM D-Luciferin in reaction buffer (25 mM Glycylglycine, 15 mM MgSO4, 4 mM EDTA, 15 mM Potassium phosphate pH 7.8, 1 mM DTT, and 1 mM Coenzyme A). Luminescence was immediately recorded with Biotek Synergy Mx microplate reader under gain setting of 135 and integration time of 1 second. Luminscence readings were plotted against Protein Kinase A (PKA) concentration. Unit concentrations of PKA which fall within the linear range of the curve can be utilized to assess the inhibitory or activating potential of small molecular compounds.

What is claimed is:

1. A method for detecting ATP in a sample comprising:
   a. contacting an isolated protein having the amino acid sequence as set forth in SEQ ID NO: 4 with a sample solution containing D-luciferin, one or more ATPase inhibitors and an unknown amount of ATP, and
   b. measuring light emitted from said sample, wherein the amount of light detected is proportional to the ATP concentration of the sample.

2. The method of claim 1, further comprising the step of adding a known concentration of ATP to the sample.

3. The method of claim 1, wherein the sample solution further comprises a cell lysing agent selected from the group consisting of Triton X-100, glycerol, TCA, DMSA, CTAB, and ethanol.

4. The method of claim 1, wherein the sample solution further comprises NaF.

5. The method of claim 1, wherein the sample solution further comprises an enzyme stabilizing agent selected from the group consisting of bovine serum albumin, gelatin, and a detergent.

6. A method of measuring cell viability within a sample population of cells by detecting ATP using the method of claim 1, wherein said sample solution further comprises a cell lysing reagent and a detergent and wherein the amount of light detected is proportional to the viability of the cells within the population.

7. A method of measuring cell proliferation within a sample population of cells by detecting ATP using the method of claim 1, wherein said sample solution further comprises a cell lysing reagent and a detergent and wherein the amount of light detected is proportional to the cell growth and proliferation of the cells within the population.

8. A method of measuring a second enzyme within a sample by detecting ATP using the method of claim 1, wherein said D-luciferin is a luciferin analog further comprises a pendant group specific for said second enzyme wherein the amount of light detected is proportional to the second enzyme concentration of the sample.

9. The method of claim 8, wherein said solution further comprises a component selected from the group consisting of a cell lysing reagent, enzyme stabilizing reagent and a detergent.

10. The method of claim 8, wherein said luciferin analog is selected from the group consisting of D-luciferin-6-O-β-D-glycopyranoside, D-luciferin-6-O amino acid, D-luciferin-4-O-amino acid, D-luciferin-6-O-methyl ether, D-luciferin-6-O-phosphate, D-luciferin-6-O-sulfate and D-luciferin-6-O-α-D-glycopyranoside.

11. The method of claim 8, wherein said second enzyme is selected from the group consisting of β-glycosidase, a peptidase, a protease, cytochrome P450, alkaline phosphatase, acid phosphatase, aryl sulfatase, α-glycosidase and kinase.

12. A method of measuring cytotoxicity within a sample population of cells by detecting ATP using the method of claim 1, wherein said light detecting step is conducted before addition of a cytotoxic agent and at least one hour after addition of said cytotoxic agent, and wherein said method further comprises the step of comparing the amount of light emitted before and after the addition of said cytotoxic agent.

* * * * *